US011609632B2

(12) United States Patent
Lee et al.

(10) Patent No.: US 11,609,632 B2
(45) Date of Patent: Mar. 21, 2023

(54) BIOSIGNAL-BASED AVATAR CONTROL SYSTEM AND METHOD

(71) Applicant: KOREA INSTITUTE OF SCIENCE AND TECHNOLOGY, Seoul (KR)

(72) Inventors: Song Joo Lee, Seoul (KR); Hyung Min Kim, Seoul (KR); Laehyun Kim, Seoul (KR); Keun Tae Kim, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 477 days.

(21) Appl. No.: 16/698,380

(22) Filed: Nov. 27, 2019

(65) Prior Publication Data
US 2021/0055794 A1 Feb. 25, 2021

(30) Foreign Application Priority Data

Aug. 21, 2019 (KR) ........................ 10-2019-0102367

(51) Int. Cl.
G06F 3/01 (2006.01)
G16H 40/63 (2018.01)
(Continued)

(52) U.S. Cl.
CPC .............. G06F 3/015 (2013.01); A61B 5/375 (2021.01); A61B 5/389 (2021.01); G06F 3/016 (2013.01);
(Continued)

(58) Field of Classification Search
CPC .... G06F 3/017; G06F 3/04883; G06F 3/0487; G06F 3/0488; G06F 3/04886; G06F 2203/04808
See application file for complete search history.

(56) References Cited

U.S. PATENT DOCUMENTS 8,033,996 B2 * 10/2011 Behar .................. A61B 5/0205 128/920
10,532,000 B1 * 1/2020 De Sapio ........... A63B 24/0062
(Continued)

FOREIGN PATENT DOCUMENTS

KR 10-2013-0116886 A 10/2013
KR 10-2015-0057424 A 5/2015
(Continued)

Primary Examiner — William Lu
(74) Attorney, Agent, or Firm — Birch, Stewart, Kolasch & Birch, LLP

(57) ABSTRACT

A biosignal-based avatar control system according to an embodiment of the present disclosure includes an avatar generating unit that generates a user's avatar in a virtual reality environment, a biosignal measuring unit that measures the user's biosignal using a sensor, a command determining unit that determines the user's command based on the measured biosignal, an avatar control unit that controls the avatar to perform the command, an output unit that outputs an image of the avatar in real-time, and a protocol generating unit for generating a protocol that provides predetermined tasks, and determines if the avatar performed the predetermined tasks. According to an embodiment of the present disclosure, it is possible to provide feedback in real-time by understanding the user's intention through analysis of biosignals and controlling the user's avatar in a virtual reality environment, thereby improving the user's brain function and motor function.

15 Claims, 4 Drawing Sheets

(51) Int. Cl.
*A61B 5/375* (2021.01)
*A61B 5/389* (2021.01)

(52) U.S. Cl.
CPC ............ *G06F 3/017* (2013.01); *G16H 40/63* (2018.01); *G06F 2203/011* (2013.01)

(56) References Cited

U.S. PATENT DOCUMENTS

| | | | | |
|---|---|---|---|---|
| 2002/0188217 | A1* | 12/2002 | Farwell | A61B 5/377 600/544 |
| 2007/0050715 | A1* | 3/2007 | Behar | G16H 40/67 600/300 |
| 2009/0069707 | A1* | 3/2009 | Sandford | A61B 5/165 600/545 |
| 2009/0124920 | A1* | 5/2009 | Patterson | A61B 5/375 600/544 |
| 2011/0118877 | A1* | 5/2011 | Hwang | G06F 3/017 901/50 |
| 2013/0324857 | A1* | 12/2013 | Kurillo | A61B 5/7465 600/595 |
| 2014/0079314 | A1* | 3/2014 | Yakubovich | G06V 10/7625 382/155 |
| 2014/0336473 | A1* | 11/2014 | Greco | A61B 5/7225 600/509 |
| 2015/0012111 | A1* | 1/2015 | Contreras-Vidal | A61B 5/369 623/25 |
| 2015/0157235 | A1* | 6/2015 | Jelen | A61B 5/291 600/383 |
| 2015/0313496 | A1* | 11/2015 | Connor | A61B 5/369 600/301 |
| 2016/0206207 | A1* | 7/2016 | Avila | A61B 5/4504 |
| 2016/0235323 | A1* | 8/2016 | Tadi | A61B 5/1128 |
| 2016/0320840 | A1* | 11/2016 | Hwang | H04R 1/1041 |
| 2017/0273601 | A1* | 9/2017 | Wang | A61B 5/1118 |
| 2018/0232051 | A1* | 8/2018 | Wu | G06V 40/23 |
| 2018/0336973 | A1* | 11/2018 | Tadi | G06F 3/015 |
| 2020/0301402 | A1* | 9/2020 | Song | G05B 19/0423 |
| 2020/0310539 | A1* | 10/2020 | Barachant | G06F 3/011 |
| 2020/0401224 | A1* | 12/2020 | Cotton | A61B 5/30 |

FOREIGN PATENT DOCUMENTS

| | | |
|---|---|---|
| KR | 10-2015-0140043 A | 12/2015 |
| KR | 10-2018-0036503 A | 4/2018 |
| KR | 10-1848478 B1 | 4/2018 |
| KR | 10-2018-0083252 A | 7/2018 |
| KR | 10-2000231 B1 | 7/2019 |
| WO | WO 2012/061804 A1 | 5/2012 |
| WO | WO 2014/142962 A | 9/2014 |
| WO | WO 2015/186925 A1 | 12/2015 |
| WO | WO 2017-031089 A1 | 2/2017 |

* cited by examiner

BIOSIGNAL-BASED AVATAR CONTROL SYSTEM AND METHOD

DESCRIPTION OF GOVERNMENT-FUNDED RESEARCH AND DEVELOPMENT

Institute for Information & Communications Technology Promotion (IITP) grant funded by the Korea government (MSIT) (2017-0-00432, Development of non-invasive integrated BCI SW platform to control home appliance and external devices by user's thought via AR/VR interface)

CROSS-REFERENCE TO RELATED APPLICATION

This application claims priority to Korean Patent Application No. 10-2019-0102367, filed on Aug. 21, 2019, and all the benefits accruing therefrom under 35 U.S.C. § 119, the contents of which in its entirety are herein incorporated by reference.

BACKGROUND

1. Field

The present disclosure relates to a biosignal-based avatar control system and method, and more particularly, to a system and method that understand a user's intention by measuring and analyzing biosignals such as electroencephalography (EEG), electromyogram (EMG) and electrooculogram (EOG) signals, and control the user's avatar in a virtual reality environment based on the user's intention, thereby providing feedback in real-time.

2. Description of the Related Art

Recently, technologies that control electronic devices or exoskeleton robots using human biosignals are being intensively studied. Among them, brain-computer interface (BCI) measures a user's brainwave through electroencephalography (EEG) and generates a control signal corresponding to the brainwave to control a device, and it can be used in various industrial fields, for example, cognition related research, motor rehabilitation, exoskeleton robots or electric wheelchairs for patients paralyzed in spine.

Further, with the development of BCI technology, interaction with an object in a virtual reality environment using EEG is developed. The virtual reality is technology that realizes a new virtual space on a computer and outputs it to an output device such as a monitor or a head-mounted display, and it realizes a space in which a user can experience many sensory phenomena including a sense of vision in a virtual situation, to provide a sense of realistic space to the user. The virtual reality provides virtual space and activities beyond the visual and physical limitations.

More recently, there are gradually growing trends of training programs for virtual training in a similar environment to real motion. In the case of cognitive and motor rehabilitation programs, there are reports about research results that cognitive and motor abilities of patients with neurological impairment can be improved through EEG signal-based motor imagery.

This is improvements in brain function and motor function using a sort of neurofeedback. The neurofeedback refers to a biofeedback technique that regulates behavior patterns while observing brainwaves, by informing a patient of his/her current brainwave state, setting a target brainwave state and training the patent for how to regulate in order to reach the target brainwave state. This is based on the principle that the human mind has a self-control function of regulating in a behavioral, cognitive and physiological manner. For example, an ADHD patient's brainwaves are measured and displayed, and in the patient's attempts to change the brainwaves by changing his/her mental state, stimuli are displayed on the screen or sound emits, so that the patient learns self-control by positive reinforcement, and this training may be repeatedly performed to obtain a long-term treatment effect of neuroplasticity.

However, there are not so many developed treatment systems or training systems combined with virtual reality technology and neurofeedback. In addition, earlier technology usually focuses only on EEG signals, and technology that controls avatars or objects in virtual reality using the entire biosignal including an EEG signal, or systems that can operate in an integrated manner for evaluation and training have never been published.

SUMMARY

The present disclosure is directed to providing a system for evaluating a user's biosignal characteristics or enhancing the user's biosignal, by understanding the user's intention through measurement and analysis of biosignals such as electroencephalogram (EEG), electromyogram (EMG) and electrooculogram (EOG) signals, and controlling the user's avatar in a virtual reality environment based on the user's intention, thereby providing feedback in real-time.

A biosignal-based avatar control system according to an embodiment of the present disclosure includes an avatar generating unit that generates a user's avatar in a virtual reality environment, a biosignal measuring unit that measures the user's biosignal using a sensor, a command determining unit that determines the user's command based on the measured biosignal, an avatar control unit that controls the avatar to perform a motion corresponding to the command, an output unit that outputs an image of the avatar performing the motion in real-time, and a protocol generating unit for generating a protocol that provides predetermined tasks that can be performed by controlling the avatar's motion, and determines if the avatar performed the predetermined tasks.

In an embodiment, the protocol may include an evaluation protocol for evaluating the user's biosignal characteristics or a training protocol for enhancing the user's biosignal.

In an embodiment, the biosignal may include at least one of an electroencephalogram (EEG) signal, an electromyogram (EMG) signal and an electrooculogram (EOG) signal.

In an embodiment, the speed of the motion or magnitude of rotation of the avatar may be controlled based on an amplitude of the biosignal.

In an embodiment, the command determining unit may process the measured biosignal through frequency filtering, spatial filtering, feature selection, and classification, and determine a command corresponding to a result value of the processing.

A biosignal-based avatar control method according to an embodiment is performed by a processor, and includes generating a user's avatar in a virtual reality environment, receiving the user's biosignal from a sensor, determining the user's command based on the biosignal, controlling the avatar to perform a motion corresponding to the command, outputting an image of the avatar performing the motion in real-time, and providing a protocol that provides predetermined tasks that can be performed by controlling the avatar's motion, and determines if the avatar performed the predetermined tasks.

In an embodiment, the determining the user's command based on the measured biosignal may include processing the measured biosignal through frequency filtering, spatial filtering, feature selection and classification, and determining a command corresponding to a result value of the processing.

In an embodiment, the protocol may include an evaluation protocol for evaluating the user's biosignal characteristics or a training protocol for enhancing the user's biosignal.

In an embodiment, the biosignal may include at least one of an EEG signal, an EMG signal and an EOG signal.

In an embodiment, the determining the user's command based on the measured biosignal may include processing the measured biosignal through frequency filtering, spatial filtering, feature selection and classification, and determining and executing a command corresponding to a result value of the processing.

In an embodiment, the speed of the motion or magnitude of rotation of the avatar may be controlled based on an amplitude of the biosignal.

There may be provided a computer program stored in a computer-readable recording medium, for performing the biosignal-based avatar control method according to an embodiment.

According to an embodiment of the present disclosure, it is possible to provide feedback in real-time by understanding the user's intention through measurement and analysis of biosignals such as electroencephalogram (EEG), electromyogram (EMG) and electrooculogram (EOG) signals, and controlling the user's avatar in a virtual reality environment based on the user's intention.

In addition, the system according to an embodiment provides an evaluation/training protocol for evaluating the user's biosignal characteristics or enhancing the user's biosignal, by providing predetermined tasks that can be performed by controlling the avatar's movement, and determining if the avatar performed the predetermined tasks. Through this biofeedback system, it is possible to improve the user's brain function and motor function and obtain a long-term treatment effect.

DETAILED DESCRIPTION

While embodiments are hereinafter described in detail with reference to the accompanying drawings and disclosure in the accompanying drawings, the intended scope is not limited or restricted by the embodiments.

The terms as used herein are general terms selected as those being now used as widely as possible in consideration of functions, but they may vary depending on the intention of those skilled in the art or the convention or the emergence of new technology. Additionally, in certain cases, there may be terms arbitrarily selected by the applicant, and in this case, the meaning will be described in the corresponding description part of the specification. Accordingly, it should be noted that the terms used herein should be interpreted based on the substantial meaning of the terms and the context throughout the specification, rather than simply the name of the terms.

Additionally, the embodiment described herein may have aspects of entirely hardware, partly hardware, and partly software, or entirely software. The term unit", "module", "device", "server" or "system" used herein refers to computer-related entity such as hardware, hardware, and software in combination, or software. For example, the unit, module, device, server or system may refer to hardware that makes up a platform in part or in whole and/or software such as an application for operating the hardware.

Hereinafter, exemplary embodiments will be described in more detail with reference to the accompanying drawings.

A Biosignal-Based Avatar Control System

Figure 1:
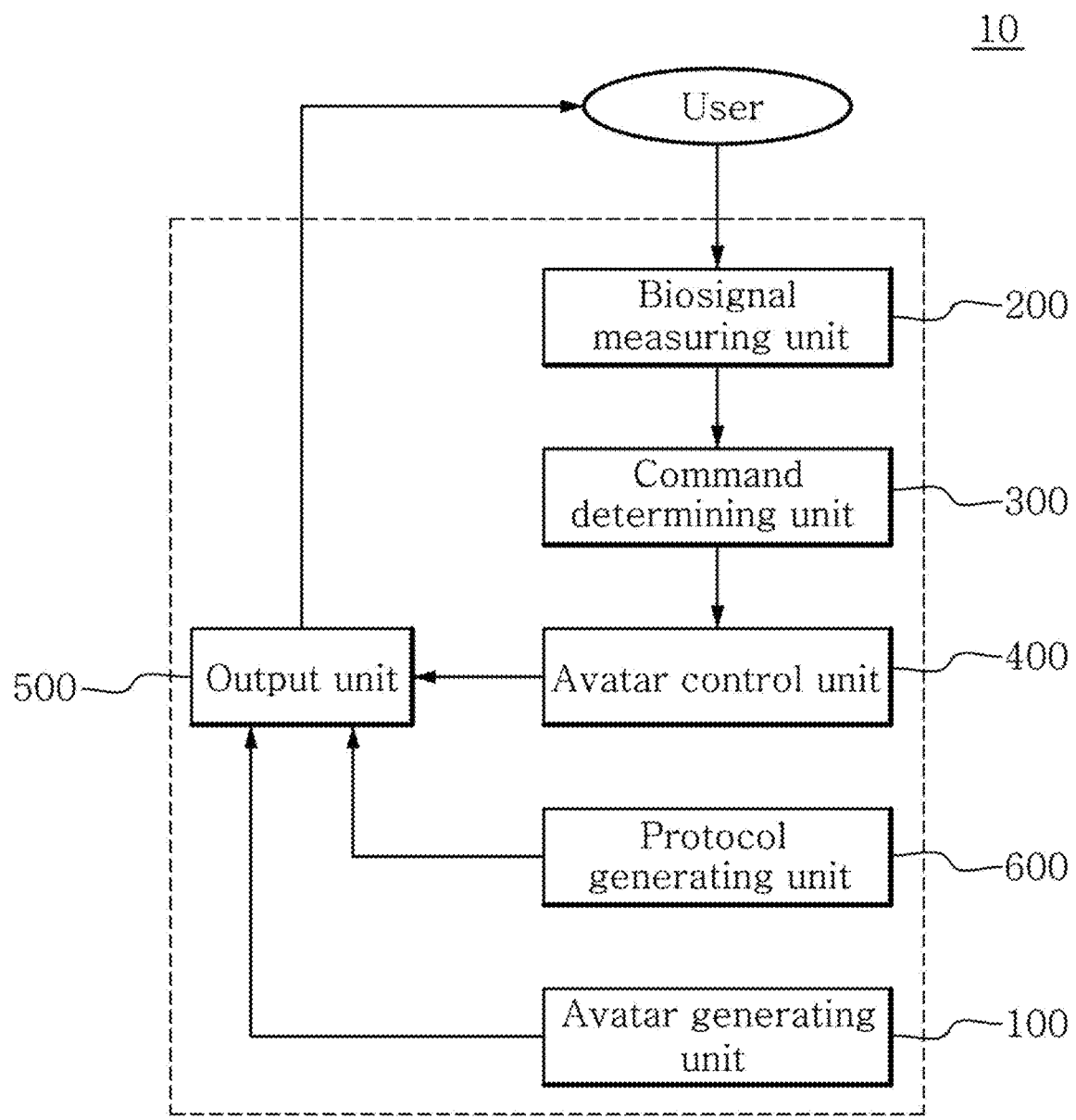
FIG. 1 is an architecture diagram showing a biosignal-based avatar control system according to an embodiment.

FIG. 1 is an architecture diagram showing a biosignal-based avatar control system according to an embodiment. Referring to FIG. 1, the avatar control system 10 includes an avatar generating unit 100, a biosignal measuring unit 200, a command determining unit 300, an avatar control unit 400, an output unit 500 and a protocol generating unit 600. Hereinafter, the roles and functions of each element will be described in detail.

The avatar generating unit 100 generates a user's avatar in a virtual reality environment. In the specification, the avatar refers to a virtual character that can be controlled according to the user's command in virtual reality created as a virtual space by computer programming, not in the real world. The avatar looks like a human having a similar shape to the user to improve the user's immersion and provide smooth biofeedback but is not limited to a specific shape.

In an embodiment, the avatar may be automatically generated based on the measured biosignal. For example, the user's heartbeat change or face temperature change may be detected and the avatar's facial color or expression and pose may be changed accordingly, or the user's gaze direction or blink may be detected by measuring an electrooculogram (EOG) signal and the avatar's gaze direction may be represented accordingly. Appropriately changing the avatar's shape or attitude in a virtual environment according to the user's biosignal may improve realism and immersion in virtual reality.

The avatar generated in the virtual reality environment performs a motion corresponding to a command determined based on the user's biosignal as described below. Using this, the user may control the avatar in virtual reality to perform a specific motion by sending the biosignal without actually performing the motion, and execute an evaluation protocol or a training protocol provided by the program.

The biosignal measuring unit 200 measures the user's biosignal using a sensor. In an embodiment, the biosignal may include an electroencephalogram (EEG) signal, an electromyogram (EMG) signal, and an electrooculogram (EOG) signal, and in addition to the biosignal described herein, a variety of biosignals may be measured and used.

The EEG signal is the electrical signal recording of potential generated by the cerebral cortex and may be measured using an electrode sensor attached to the user's head. As an EEG signal is generated from a specific part of the brain in a specific situation in which human experiences, an EEG signal of desired characteristics (wavelength, frequency, intensity, etc.) may be generated by applying any type of sensory stimulus or stimulating the brain by the user's imagination, and may be matched with a specific command and a control signal to control a device.

The EMG signal is the electrical signal recording of action potential generated by muscles and may be measured by attaching electrodes to the user's skin surface or directly inserting a needle into the muscle. In the same way as the EEG signal, an EMG signal of desired characteristics may be generated by applying a sensory stimulus to a specific body part of the user's intentional muscle activation and may be matched with a specific command and a control signal to control a device.

The EOG signal is the electrical signal recording of a potential difference caused by changes such as contraction or relaxation of muscles around eyes and may be measured by attaching electrodes to the user's skin around the eyes. As a specific EOG signal is generated by a specific eye movement, the user's eye movement may be tracked from the EOG signal measurement, and in the same way as EEG and EMG, may be matched with a specific command and a control signal to control a device.

The command determining unit 300 receives the biosignal measured by the biosignal measuring unit 200 and determines the user's corresponding command by processing the biosignal through the processor. Related information necessary to determine the command, such as an analysis algorithm or a lookup table, may be stored in memory together with a biosignal based control program.

Figure 2:
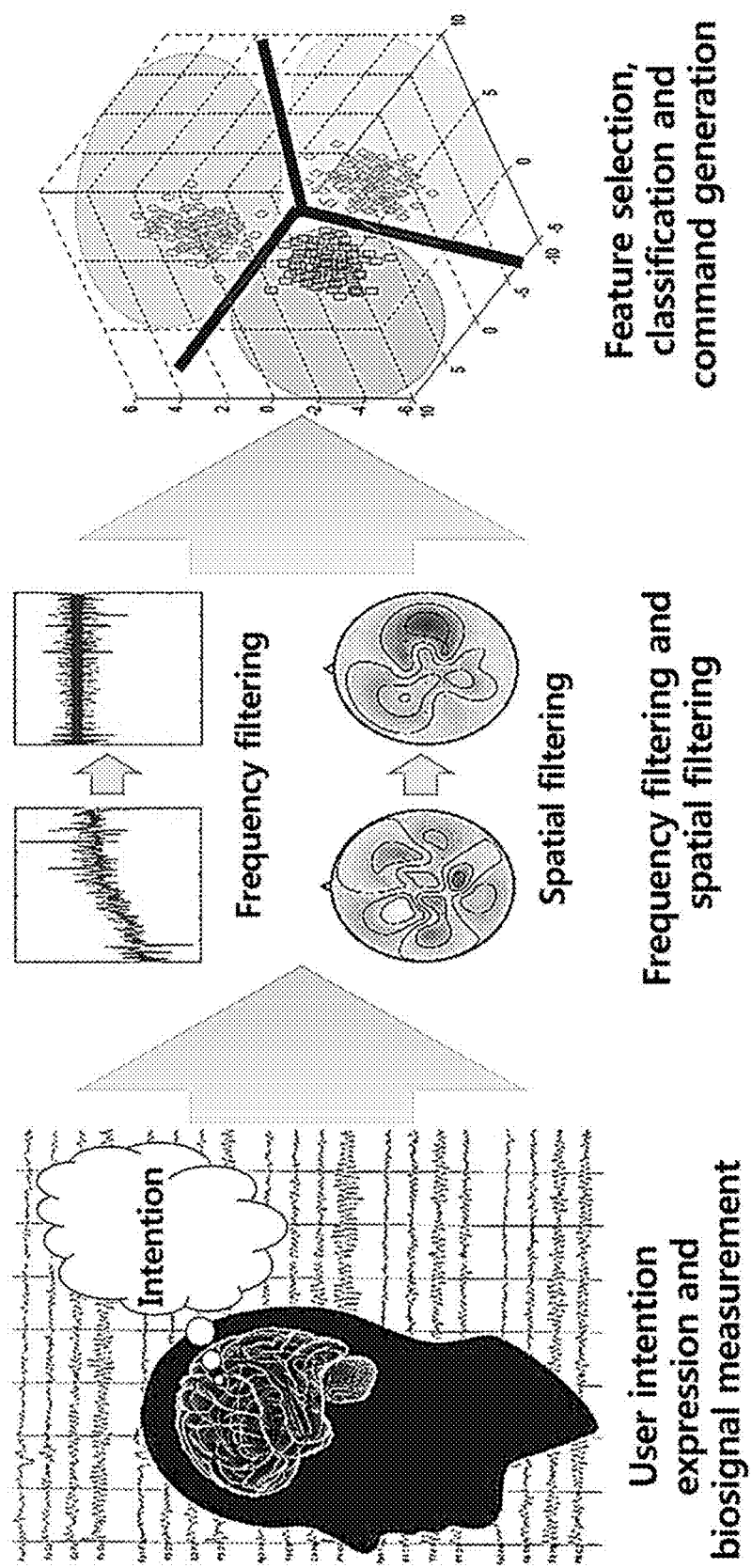
FIG. 2 shows a signal processing process of determining a command based on a biosignal in a biosignal-based avatar control system according to an embodiment.

FIG. 2 shows a signal processing process of determining the command based on the biosignal in the biosignal-based avatar control system according to an embodiment. Referring to FIG. 2, the command determining unit 300 may process the measured biosignal through frequency filtering, spatial filtering, feature selection, and classification.

The command determining unit 300 may perform frequency filtering of the biosignal through the processor. A low-pass filter may be used to remove high-frequency noise, a band-pass filter may be used to select a specific frequency domain, or a band-stop filter may be used to remove a specific frequency domain.

The biosignal having the selected specific frequency goes through spatial filtering. This is to maximize the feature based on the spatial location of the body to which the electrode for measuring biosignals is attached. A weight may be given to the specific location, i.e., the specific electrode through spatial filtering, and through this, in recognizing the user's specific command, a feature vector is extracted by giving a weight to the largest spatially influential part. For example, when the user has a certain intention, it is possible to extract a feature vector by giving a weight to a specific location (electrode) having a great change due to a high relevance to the corresponding intention by the application of a spatial filtering algorithm, for example, Common Average Reference (CAR), Common Spatial Pattern (CSP), to the biosignal having passed through frequency filtering.

The command determining unit 300 extracts the feature vector based on data power calculated including a log value and a variance value for the corresponding frequency of the filtered signal. For example, the processor may quantitatively analyze a ratio of the signal component of the specific frequency occupied on signal data based on the fast Fourier transform (FFT).

Besides, the feature vector may be extracted by calculating a mean, a deviation, Root mean square (RMS), skewness, kurtosis and Dominant frequency (DF) by the application of a signal processing function to the biosignal, and the extracted feature vector data may be used to determine the corresponding user's command.

When pre-processing of the biosignal is completed, the command determining unit 300 may generate a plurality of classifiers through a classifier generation module. The processor may generate the classifiers based on a plurality of classification algorithms. The plurality of classifiers classifies biosignal data and determines if the data corresponds to a specific class.

A command determination module selects a motion corresponding to real-time biosignal data from a plurality of motions based on the classifiers, and finally, determines the user's command. In detail, the processor may calculate each motion for real-time input biosignal data as output values such as probabilities or scores based on the biosignal classifiers, select a motion having a highest probability or score, and determine a command.

According to embodiments, various types of commands may be pre-stored to match the biosignals. For example, further to a command for simply moving the avatar forward, rearward, leftward and rightward, a command such as sitting down/standing, or a joint-related movement such as lifting up and down the feet and bending or straightening the knees may be designated as the command. As opposed to the existing gesture capture based avatar control method, the present disclosure may simultaneously acquire various types of biosignals including an EEG signal and an EMG signal, and match them to detailed motion commands, thereby realizing diverse and natural motions in virtual reality. A signal processing algorithm for understanding the user's intention for each command and reducing the failure rate is the same as described above.

The avatar control unit 400 receives the determined command and controls the avatar to perform a motion corresponding to the command through the processor. The user's motion intention is converted to a state and determined as a command. (e.g., start 1, stop 2, turn left 3, turn right 4, stand 5, etc.)

Even for the same motion, the magnitude of rotation and the movement speed may be different, and in addition to the state of the command, may be adjusted according to the amplitude of the biosignal. For example, when an EEG signal having a specific frequency or an EMG signal generated at a specific part is detected, and the signal of the corresponding frequency and the corresponding part matches a "go forward" command, the avatar control unit 400 controls the avatar to go forward. In this instance, as the amplitude of the EEG signal or the EMG signal is higher, the avatar may go forward at a faster speed, and as the amplitude is lower, the avatar may go forward at a slower speed.

Different feedbacks may be provided for the same motion depending on the intensity of the biosignal and may be used in evaluating the user's biosignal characteristics or training for enhancing the user's biosignal.

The output unit 500 is an output device for outputting an image of the avatar performing the motion in real-time, for example, a TV, a monitor, and a head-mounted display (HMD). In an embodiment, the output unit 500 may include a display with a light-emitting diode (LED), an organic LED (OLED), a light-emitting polymer (LEP), an electroluminescent (EL) device, a field-emission display (FED), or a polymer LED (PLED).

In an exemplary embodiment, the output unit 500 may be the HMD device that can be worn on the head. The HMD device is a next-generation display device that is worn on the user's head and allows the user to see images through displays corresponding to two eyes. In general, the inclusion of an IMU sensor makes it possible to synchronize the user's head movement through a rotation value. Through this, the user can feel more full immersion in an augmented reality or virtual reality environment than those when the user watches on the existing monitor devices.

Figure 3:
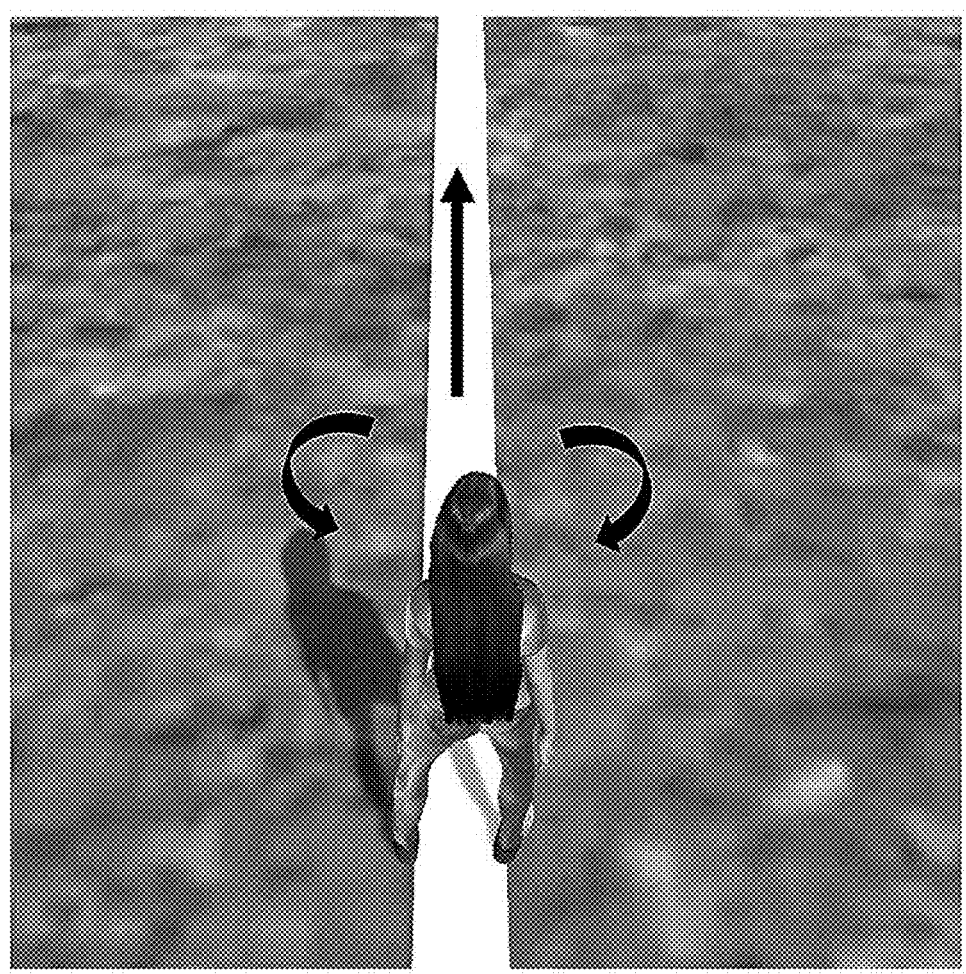
FIG. 3 shows the real-time output of an image of an avatar performing a motion in a biosignal-based avatar control system according to an embodiment.

As shown in FIG. 3, the image of the avatar performing the motion may be outputted in real-time. As shown, the user's avatar may perform a motion, for example, going forward or rotating to left or right, according to the control command. As the user watches the real-time output image of the avatar performing the motion based on the biosignal, the user can obtain immediate feedback.

The protocol generating unit 600 generates a protocol that provides predetermined tasks that can be performed by controlling the motion of the avatar and determines if the avatar performed the predetermined tasks. In an embodiment, the protocol includes an evaluation protocol for evaluating the user's biosignal characteristics or a training protocol for enhancing the user's biosignal.

The evaluation/training protocol as used herein refers to a program for virtual training in a similar environment to a real motion in a virtual reality environment. Through the brain signal based motor imagery, it is possible to improve the cognitive abilities of patients with mental illness or motor abilities of patients with neurological impairment. These are improvements in brain function and motor function using the biofeedback technique. In summary, behavior patterns may be regulated by setting a target brainwave state, eye movement, and muscle contraction/relaxation and training the user for how to regulate in order to reach the target brainwave state, and may iterate to improve cognitive and motor abilities.

In an embodiment, the evaluation protocol may instruct the user to generate a specific biosignal, and measure and score the number of times or intensity of the specific biosignal generated for a preset time. Alternatively, the evaluation protocol may evaluate and score the accuracy of the motion of the avatar according to the biosignal. Inducing the avatar to move may give greater motivation to the user than detecting and scoring the biosignal.

For example, the evaluation protocol may apply a sensory stimulus (visual, auditory, kinesthetic) to the user through the display to induce the generation of a specific brainwave or instruct the application of a force to a specific muscle, and when the user generates a biosignal in response, control the avatar according to the biosignal, and evaluate the characteristics of the biosignal by scoring the accuracy of the motion performed by the avatar.

In an embodiment, the training protocol instructs the user to generate a specific biosignal to control the avatar. For example, there may be provided a training program that enhances the biosignal by outputting in real-time images of the avatar being controlled by the biosignal to stimulate the user. The instruction motion of the avatar given by the program requires stepwise high-level motions, for example, running on a preset track, rotation and obstacle avoidance as shown in FIG. 3 to induce gradual improvement in the user's ability to generate biosignals. With training, the user can activate brainwaves of desired characteristics, and control the muscles of a desired body part or control eye movements, leading to improvements in cognitive and motor abilities.

A Biosignal-Based Avatar Control Method

Figure 4:
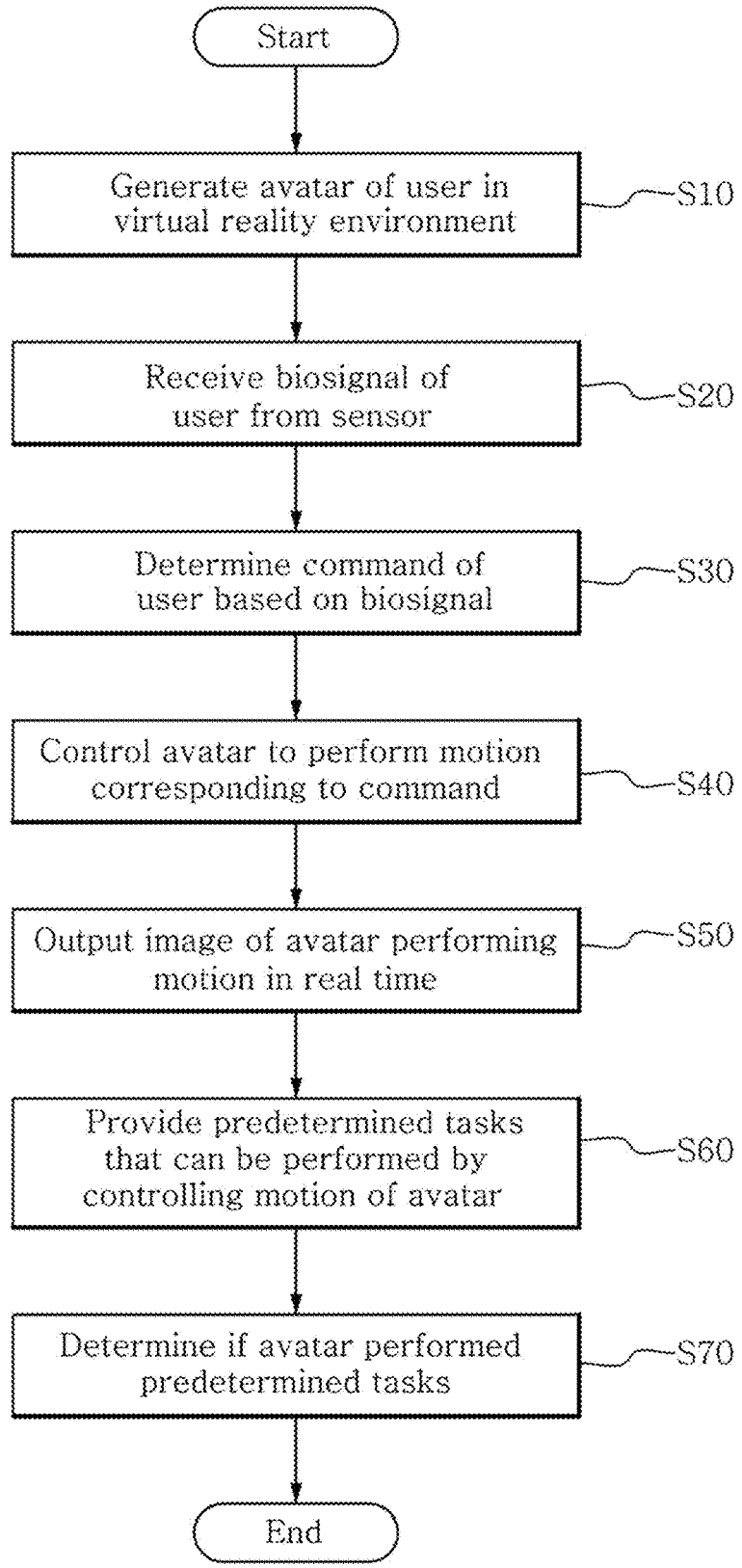
FIG. 4 is a flowchart showing a biosignal-based avatar control method according to an embodiment.

FIG. 4 is a flowchart showing a biosignal-based avatar control method according to an embodiment. Each step (S10 to S70) shown in FIG. 4 is not necessarily in a sequential or essential relationship. That is, some steps may be omitted or performed in different orders.

Referring to FIG. 4, first, the step of generating a user's avatar in a virtual reality environment is performed (S10). In an embodiment, the avatar may be automatically generated based on a measured biosignal. For example, the user's heartbeat change or face temperature change may be detected and the avatar's facial color or expression and pose may be changed accordingly, or the user's gaze direction or blink may be detected by measuring an EOG signal and the avatar's gaze direction may be represented accordingly. Appropriately changing the avatar's shape or attitude in a virtual environment according to the user's biosignal may improve realism and immersion in virtual reality.

Subsequently, the step of receiving the user's biosignal from a sensor is performed (S20). In an embodiment, the biosignal may include an EEG signal, an EMG signal, and an EOG signal, and in addition to the biosignals described herein, a variety of biosignals may be measured and used. The features and measuring methods of each biosignal are the same as described above, and redundant descriptions are omitted herein.

Subsequently, the step of determining the user's command based on the biosignal is performed (S30). In an embodiment, the step of determining the user's command based on the measured biosignal includes the step of processing the measured biosignal through frequency filtering, spatial filtering, feature selection and classification, and the step of determining a command corresponding to a result value of the processing. Related information necessary to determine the command, for example, an analysis algorithm or lookup table, may be stored in memory together with a biosignal based control program.

According to embodiments, various types of commands may be pre-stored to match the biosignals. For example, further to a command for simply moving the avatar forward, rearward, leftward and rightward, a command such as sitting down/standing, or a joint-related movement such as lifting up and down the feet and bending or straightening the knees may be designated as the command. As opposed to the existing gesture capture based avatar control method, the present disclosure may simultaneously acquire various types of biosignals including an EEG signal and an EMG signal, and match them to detailed motion commands, thereby realizing diverse and natural motions in virtual reality.

Subsequently, the step of controlling the avatar to perform a motion corresponding to the command is performed (S40). The user's motion intention is converted to a state and determined as a command (e.g., start 1, stop 2, turn left 3, turn right 4, stand 5, etc.). Even for the same motion, the extent and speed of the rotation may be different, and in addition to the state of the command, may be adjusted according to the amplitude of the biosignal as described above. Different feedbacks may be provided for the same motion depending on the intensity of the biosignal and used in evaluating the characteristics of the user's biosignal or training for enhancing the user's biosignal.

Subsequently, the step of outputting an image of the avatar performing the motion in real-time is performed (S50). The avatar's motion, training tasks, whether the tasks were performed and evaluation scores may be displayed together on an output device, for example, TV, a monitor, and the HMD. As shown in FIG. 3, the image of the avatar performing the motion may be outputted in real-time. As shown, the user's avatar may perform a motion, for example, going forward or rotating to left or right, according to the control command, and when seeing this, the user may obtain immediate feedback.

Subsequently, the step of providing predetermined tasks that can be performed by controlling the avatar's motion (S60), and the step of determining if the avatar performed the predetermined tasks (S70) are performed. The protocol includes an evaluation protocol for evaluating the user's biosignal characteristics or a training protocol for enhancing the user's biosignal. The detailed description and examples of the evaluation/training protocol are the same as described above, and redundant descriptions are omitted herein.

The biosignal-based avatar control method according to an embodiment may be implemented in the form of applications or program commands that can be executed through various computer components and may be recorded in computer-readable recording media. The computer-readable recording media may include program commands, data files, and data structures, alone or in combination.

The program commands recorded in the computer-readable recording media may be specially designed and configured for the present disclosure and may be those known and available to those having ordinary skill in the field of computer software.

Examples of the computer-readable recording media include hardware devices specially designed to store and execute program commands, for example, magnetic media such as hard disk, floppy disk and magnetic tape, optical media such as CD-ROM and DVD, magneto-optical media such as floptical disk, and ROM, RAM and flash memory.

Examples of the program command include machine code generated by a compiler as well as high-level language code that can be executed by a computer using an interpreter. The hardware device may be configured to act as one or more software modules to perform the processing according to the present disclosure, or vice versa.

According to the biosignal-based avatar control system and method as described hereinabove, it is possible to provide feedback in real-time by understanding the user's intention through measurement and analysis of biosignals such as EEG, EMG and EOG signals, and controlling the user's avatar in a virtual reality environment based on the user's intention.

In addition, the system according to an embodiment may provide the evaluation/training protocol for evaluating the user's biosignal characteristics or enhancing the user's biosignal by providing predetermined tasks that can be performed by controlling the avatar's movement, and determining if the avatar performed the predetermined tasks. Through this biofeedback system, it is possible to improve the user's brain function and motor function and obtain a long-term treatment effect.

While the present disclosure has been hereinabove described with reference to the embodiments, those skilled in the art will understand that various modifications and changes may be made thereto without departing from the spirit and scope of the present disclosure defined in the appended claims.

What is claimed is:

1. A biosignal-based avatar control system, comprising:
   an avatar generator that generates a user's avatar in a virtual reality environment;
   a biosignal measuring unit that measures the user's biosignal using a sensor;
   a command determining unit that determines the user's command based on the measured biosignal;
   an avatar controller that controls the avatar to perform a motion corresponding to the command;
   an output unit that outputs an image of the avatar performing the motion in real-time; and
   a protocol generator that generates a protocol for providing predetermined tasks that can be performed by controlling the avatar's motion, and for determining whether the avatar has performed the predetermined tasks,
   wherein the protocol includes:
      an evaluation protocol for evaluating the user's biosignal characteristics, or
      a training protocol for enhancing the user's biosignal, and
   wherein the training protocol is configured to improve the user's cognitive and motor abilities to enhance the user's biosignal that controls the avatar's motion to perform the predetermined tasks.

2. The biosignal-based avatar control system according to claim 1, wherein the biosignal includes at least one of an electroencephalogram (EEG) signal, an electromyogram (EMG) signal and an electrooculogram (EOG) signal.

3. The biosignal-based avatar control system according to claim 1, wherein a speed of the motion or magnitude of rotation of the avatar is controlled based on an amplitude of the biosignal.

4. The biosignal-based avatar control system according to claim 1, wherein the command determining unit processes the measured biosignal through frequency filtering, spatial filtering, feature selection, and classification, and determines a command corresponding to a result value of the processing.

5. The biosignal-based avatar control system according to claim 1, wherein the evaluation protocol evaluates the user's biosignal characteristics based on a number of times or intensity of the user's biosignal generated for a preset time in order to control the avatar's motion to perform the tasks.

6. The biosignal-based avatar control system according to claim 1, wherein the evaluation protocol evaluates the user's biosignal characteristics based on accuracy of the tasks performed by the avatar.

7. The biosignal-based avatar control system according to claim 1, wherein the training protocol provides stepwise high-level tasks to induce gradual enhancement of the user's biosignal.

8. A biosignal-based avatar control method that is performed by a processor, the method comprising:
   generating a user's avatar in a virtual reality environment;
   receiving the user's biosignal from a sensor;
   determining the user's command based on the biosignal;
   controlling the avatar to perform a motion corresponding to the command;
   outputting an image of the avatar for performing the motion in real-time; and
   providing a protocol that provides predetermined tasks that can be performed by controlling the avatar's motion, and determines whether the avatar has performed the predetermined tasks,
   wherein the protocol includes:
      an evaluation protocol for evaluating the user's biosignal characteristics, or
      a training protocol for enhancing the user's biosignal, and
   wherein the training protocol is configured to improve the user's cognitive and motor abilities to enhance the user's biosignal that controls the avatar's motion to perform the predetermined tasks.

9. The biosignal-based avatar control method according to claim 8, wherein the biosignal includes at least one of an electroencephalogram (EEG) signal, an electromyogram (EMG) signal and an electrooculogram (EOG) signal.

10. The biosignal-based avatar control method according to claim 8, wherein the determining the user's command based on the biosignal comprises:
processing the biosignal through frequency filtering, spatial filtering, feature selection, and classification, and
determining and executing a command corresponding to a result value of the processing.

11. The biosignal-based avatar control method according to claim 8, wherein a speed of the motion or magnitude of rotation of the avatar is controlled based on an amplitude of the biosignal.

12. The biosignal-based avatar control method according to claim 8, wherein the evaluation protocol evaluates the user's biosignal characteristics based on a number of times or intensity of the user's biosignal generated for a preset time in order to control the avatar's motion to perform the tasks.

13. The biosignal-based avatar control method according to claim 8, wherein the evaluation protocol evaluates the user's biosignal characteristics based on accuracy of the tasks performed by the avatar.

14. The biosignal-based avatar control method according to claim 8, wherein the training protocol provides stepwise high-level tasks to induce gradual enhancement of the user's biosignal.

15. A non-transitory computer readable storage medium for storing therein a computer program for performing the biosignal-based avatar control method according to claim 8.

\* \* \* \* \*